US009434479B2

(12) United States Patent
Metzger, Jr.

(10) Patent No.: US 9,434,479 B2
(45) Date of Patent: Sep. 6, 2016

(54) AIRCRAFT TIRE AND RUNWAY INTERFACE FRICTION MAP CONSOLIDATION

(71) Applicant: Goodrich Corporation, Charlotte, NC (US)

(72) Inventor: Richard Paul Metzger, Jr., Troy, OH (US)

(73) Assignee: GOODRICH CORPORATION, Charlotte, NC (US)

( * ) Notice: Subject to any disclaimer, the term of this patent is extended or adjusted under 35 U.S.C. 154(b) by 395 days.

(21) Appl. No.: 14/084,298

(22) Filed: Nov. 19, 2013

(65) Prior Publication Data

US 2015/0142388 A1  May 21, 2015

(51) Int. Cl.
| | |
|---|---|
| *B64D 45/00* | (2006.01) |
| *B60T 8/17* | (2006.01) |
| *G08G 5/06* | (2006.01) |
| *G01N 19/02* | (2006.01) |
| *G08G 5/00* | (2006.01) |
| *B64C 25/42* | (2006.01) |
| *B60T 8/172* | (2006.01) |

(52) U.S. Cl.
CPC .............. *B64D 45/00* (2013.01); *B60T 8/172* (2013.01); *B60T 8/1703* (2013.01); *B64C 25/426* (2013.01); *G01N 19/02* (2013.01); *G08G 5/0008* (2013.01); *G08G 5/0021* (2013.01); *G08G 5/065* (2013.01); *B60T 2210/12* (2013.01)

(58) Field of Classification Search
CPC .. B64D 45/00; B64C 25/426; G08G 5/0008; G08G 5/0021; G08G 5/065; G01N 19/02; B60T 8/172; B60T 8/1703; B60T 2210/12
See application file for complete search history.

(56) References Cited

U.S. PATENT DOCUMENTS 4,078,845 A  3/1978 Amberg et al.

| 5,576,959 | A * | 11/1996 | Hrovat | B60T 8/172 180/197 |
|---|---|---|---|---|
| 6,473,712 | B1 * | 10/2002 | Faye | B60T 8/172 701/94 |
| 2003/0025035 | A1 | 2/2003 | Park | |
| 2004/0177671 | A1* | 9/2004 | Hurson | B60T 8/1725 73/9 |
| 2007/0095588 | A1* | 5/2007 | Mattes | B60T 8/172 180/197 |
| 2007/0132311 | A1 | 6/2007 | Giazotto | |
| 2008/0119966 | A1 | 5/2008 | Breed et al. | |
| 2008/0154445 | A1 | 6/2008 | Goodman et al. | |
| 2009/0265072 | A1 | 10/2009 | Kondou et al. | |
| 2009/0292483 | A1 | 11/2009 | Journade et al. | |
| 2010/0211279 | A1 | 8/2010 | Lingman et al. | |
| 2011/0144875 | A1 | 6/2011 | Rado | |

(Continued)

FOREIGN PATENT DOCUMENTS

| EP | 2554443 | 2/2013 |
|---|---|---|
| WO | 2011119634 | 9/2011 |

OTHER PUBLICATIONS

Final Office Action dated Dec. 10, 2015 in U.S. Appl. No. 14/084,277.
Advisory Action dated Feb. 18, 2016 in U.S. Appl. No. 14/084,277.
Office Action dated Mar. 17, 2016 in U.S. Appl. No. 14/084,277.
Preinterview First Office Action dated Mar. 25, 2015 in U.S. Appl. No. 14/084,277.

(Continued)

*Primary Examiner* — Rodney Butler
(74) *Attorney, Agent, or Firm* — Snell & Wilmer, L.L.P.

(57) ABSTRACT

In various embodiments, a method associating received coefficient of friction data to runway friction estimation map elements. Also, the method may include aggregating the received determined coefficient of friction data into a friction estimation map.

19 Claims, 8 Drawing Sheets

(56) References Cited

U.S. PATENT DOCUMENTS

| | | |
|---|---|---|
| 2011/0264300 A1 | 10/2011 | Tuononen |
| 2012/0095659 A1* | 4/2012 | Rodrigues ............ B60K 23/08 701/69 |
| 2013/0190999 A1 | 7/2013 | Rado |
| 2013/0226430 A1 | 8/2013 | Rado |
| 2015/0142217 A1 | 5/2015 | Metzger |

OTHER PUBLICATIONS

Extended European Search Report dated Mar. 20, 2015 in European Application No. 14193358.0.
First Action Interview Office Action dated Aug. 5, 2015 in U.S. Appl. No. 14/084,277.
Extended European Search Report dated Mar. 18, 2015 in European Application No. 14193341.6.

* cited by examiner

AIRCRAFT TIRE AND RUNWAY INTERFACE FRICTION MAP CONSOLIDATION

FIELD

The present disclosure relates to brake control systems, and more particularly, to a system for exploiting known runway friction characteristics.

BACKGROUND

Aircraft landing gear and aircraft wheels are typically equipped with brakes in order to stop an aircraft after landing or during a rejected take-off braking stop. Generally, a braked wheel can be described as experiencing one of four conditions; unbraked (synchronous speed), braked but not skidding (slip velocity less than critical value), skidding (slip velocity greater than critical value), or fully locked.

Historically, prior to landing, having prior knowledge of various runway conditions was not possible. Accordingly, without prior knowledge of runway conditions, brake control systems had to expend time to assess runway conditions and enact operation during braking. This time to assess braking conditions and change performance resulted in a reduction in braking performance and the potential increase to stop distances.

SUMMARY

A method for receiving, by a central processor, coefficient of friction data and slip ratio of a first series of locations along a runway. The method may include associating the coefficient of friction data to runway friction estimation map elements. The method may include receiving coefficient of friction data for a first series of locations along the runway from a first aircraft. The method may include receiving coefficient of friction data for a second series of locations along the runway from a second aircraft. Also, the method may include aggregating the received determined coefficient of friction data for the first series of locations along the runway from the first aircraft and the determined coefficient of friction data for the second series of locations along the runway from the second aircraft into a friction estimation map.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures, wherein like numerals denote like elements.

DETAILED DESCRIPTION

Figure 1:
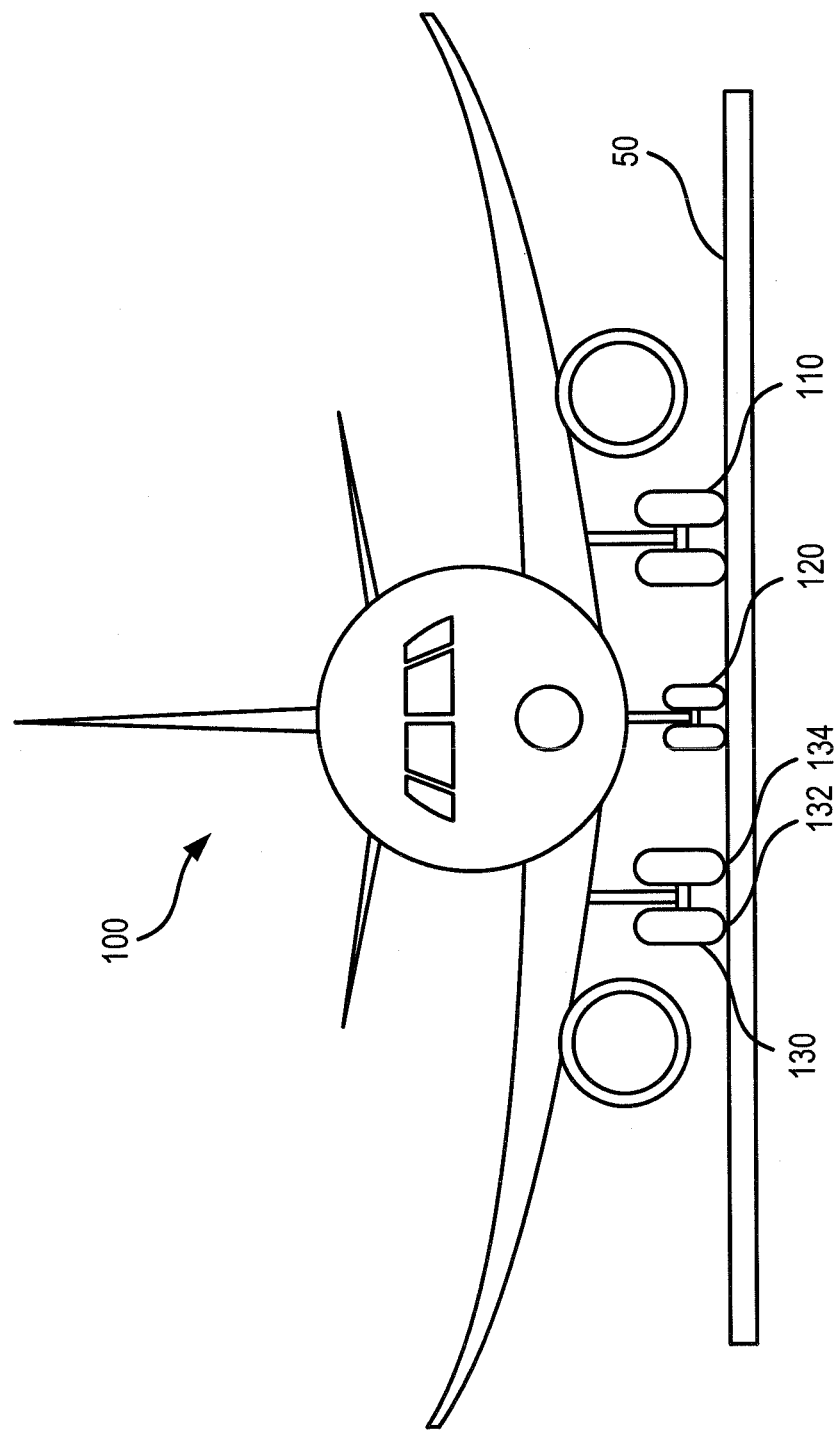
FIG. 1 illustrates, in accordance with various embodiments, a front view of an aircraft on a runway.

The detailed description of exemplary embodiments herein makes reference to the accompanying drawings, which show exemplary embodiments by way of illustration and their best mode. While these exemplary embodiments are described in sufficient detail to enable those skilled in the art to practice the disclosure, it should be understood that other embodiments may be realized and that logical, chemical, and mechanical changes may be made without departing from the spirit and scope of the disclosure. Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

In general, a tire, wheel, brake rotors and axle rotate together. The opposite of a skid event is the condition where the tire, wheel, etc., rotate freely at a speed equivalent to the translational axle speed. This equivalent speed without any deceleration is referred to as the synchronous wheel speed. As the brakes are applied, torque is generated which slows the rotational speed of the wheel. This causes the wheel to rotate at a speed slower than the synchronous speed. This difference between synchronous speed and equivalent braked speed represents the slip velocity. As the slip velocity or difference increases the tire drag force created at the tire/runway interface increases, causing the aircraft to decelerate. This drag force increases until slip velocity reaches a value dependent on tire/runway conditions. As slip velocity increases beyond this value drag force decreases. Thus, the goal of efficient antiskid control is to maintain operation near this critical slip velocity corresponding to the maximum drag force.

According to various embodiments, a map and/or a portion of a map may be produced based on substantially real-time information regarding the runway characteristics for use during a landing event. This information may include slip ratio and coefficient of friction and/or the slip ratio peak information according to position, such as according to various positions along runway 50 at various times, with brief reference to FIGS. 1 and 2).

According to various embodiments, a brake control system 101 (described in greater detail in FIG. 5) may be configured to continuously assess tire/runway 50 friction properties, detect the onset of wheel skids, and control brake torque to achieve efficient and smooth braking performance. Thus, brake control system 101 may utilize an algorithm, along with substantially real-time measured values to assist with controlling brake torque to achieve efficient and/or smooth braking performance. A history of wheel speed information, such as wheel speed information associated with one or more braking events (e.g., associated with a landing and/or braking stop), may also be used to iteratively estimate tire/runway 50 friction properties.

Referring to FIG. 1, a front view of an aircraft 100 on runway 50 is illustrated according to various embodiments. Aircraft 100 may comprise landing gear including left main landing gear ("LMLG") 110, nose landing gear ("NLG") 120, and right main landing gear ("RMLG") 130. Though a t-gear type landing gear aircraft is depicted, it should be appreciated that the concepts described herein are applicable to aircraft having multiple axle pairs per gear and aircraft with more than two main landing gears. Each gear may comprise two wheels. For example, RMLG 130 comprises right outboard wheel 132 and right inboard wheel 134. However, in various embodiments, aircraft 100 may comprise any number of gears and each gear may comprise any number of wheels. Additionally the concepts disclosed herein variously apply to two wheel aircraft (e.g. one wheel for each main landing gear).

Figure 2:
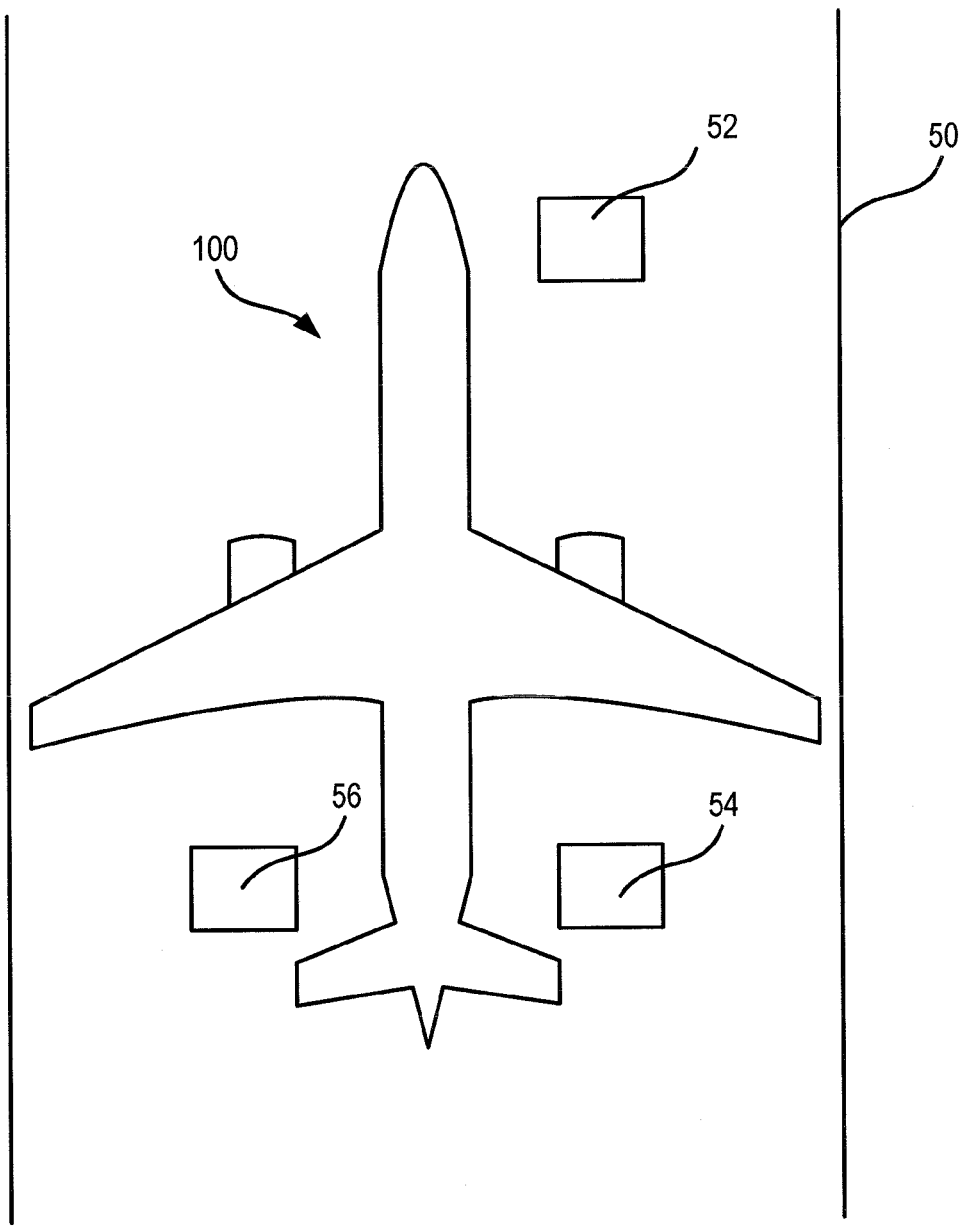
FIG. 2 illustrates, in accordance with various embodiments, a top view of an aircraft on a runway.

Referring to FIG. 2, a top view of aircraft 100 on runway 50 is illustrated according to various embodiments. Thus, in various embodiments, one or more aircraft 100 wheels may be in contact with the pavement of runway 50. Different coefficients of friction of runway 50 at various positions, such as positions 52, 54, and 56, may cause the wheels of aircraft 100 to spin up at varying rates. In various embodiments, the wheels associated with LMLG 110 may spin up faster than the wheels associated with RMLG 130 due to a higher coefficient of friction for runway 50 at one position versus another position. In various embodiments, runway 50 may comprise multiple contaminants, such as ice, mud, oil, fuel, water and/or snow, each of which may affect a measured/estimated coefficient of friction at various positions. The measured/estimated coefficient of friction at various positions along runway 50 may be time-specific. For instance, the measured/estimated coefficient of friction at various locations may change based on conditions over time.

Figure 3:
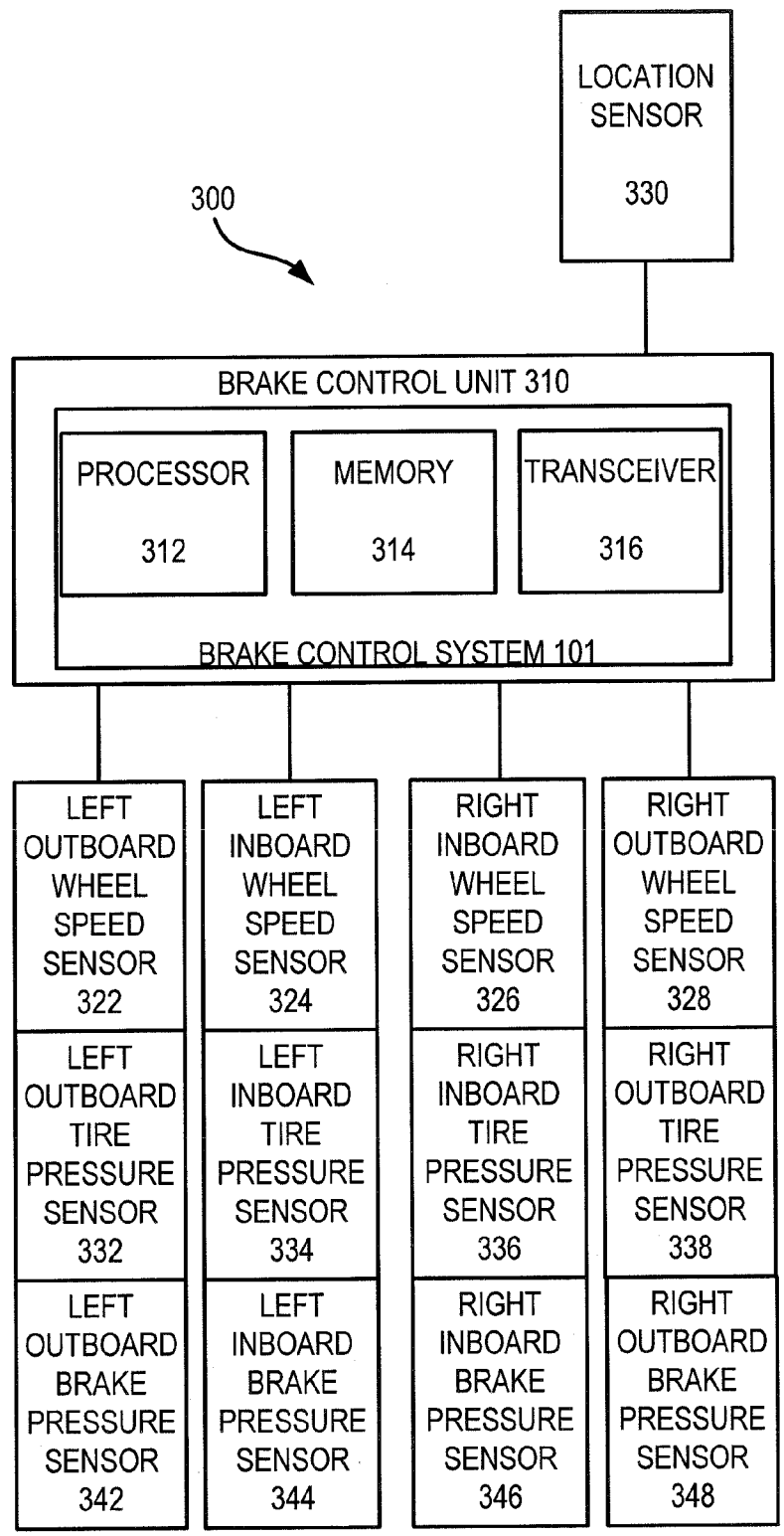
FIG. 3 illustrates, in accordance with various embodiments, a block diagram of a brake control unit.

Referring to FIG. 3, a system 300 for detecting on ground characteristics is illustrated according to various embodiments. System 300 may comprise a brake control unit (BCU) 310. A brake control system 101 may be a subsystem of brake control unit 310. Brake control system 101 may be in communication with brake control unit 310. Brake control system 101 may be communicatively coupled to left outboard wheel speed sensor 322, left inboard wheel speed sensor 324, right inboard wheel speed sensor 326 and right outboard wheel speed sensor 328. Brake control system 101 may comprise a left outboard tire pressure sensor 332, left inboard tire pressure sensor 334, right inboard tire pressure sensor 336, and right outboard tire pressure sensor 338. Tire pressure measurements may be used to infer a weight and force present on the tires at various times/locations. The tire pressure measurement may allow for an estimation of a tire spring constant. When coupled with a tire radius information and position data, a force may be estimated if not directly measured. For instance, tire pressure coupled with the tire radius derived from the distance between an aircraft touchdown and wheel speed sensor drop out positions allow for normal force estimation. The elimination of the tire pressure measurement does not prevent this estimation but may limit its fidelity.

A location sensor 330 may be coupled to brake control system 101 and/or brake control unit 310. Location sensor 330 may be a GPS unit/receiver. Location sensor 330 may be configured to determine position of aircraft 100 at each braked wheel location. Brake control unit 310 may be coupled to a transceiver 316. The various components may be electronically coupled. In various embodiments, the various components may communicate via wireless and/or wired communications. For example, wheel speed sensors 322, 324, 326, 328 may transmit, via wired and/or wireless transmission, wheel speed measurements to brake control system 101 and in turn to brake control unit 310. The wheel speed sensors, pressure sensor and tire pressure sensors may be hard wired to BCU 310. Transceiver 316 may transmit the slip ratio vs. position data and the coefficient of friction vs. position data to a central data base/processing computer. This central data base/processing computer may be a collection of each air plane's friction map for processing and/or aggregating, Brake control unit 310 and/or brake control system 101 may comprise a computing device (e.g., processor 312) and an associated memory 314. Memory 314 may comprise an article of manufacture including a tangible, non-transitory computer-readable storage medium having instructions stored thereon that, in response to execution by a computing device (e.g., processor 312), cause the computing device to perform various methods.

Wheel speed sensors 322, 324, 326, 328 may measure a wheel speed. Wheel speed sensors 322, 324, 326, 328 may comprise any device capable of measuring a wheel speed. For example, in various embodiments, wheel speed sensors 322, 324, 326, 328 may comprise electromagnetic transducers and/or fiber optic transducers. In various embodiments, the wheel speed sensors may comprise an AC sensor which uses a magnet surrounded by a pickup coil in an axle of the landing gear. In various embodiments, wheel speed sensors 322, 324, 326, 328 may comprise a DC sensor which may comprise a permanent magnet direct current generator, which outputs a voltage proportional to a rotational speed of its armature. Additionally, wheel speed sensors 322, 324, 326, 328 may detect a change in a rate of deceleration of the wheels. The processing of wheel speed to produce acceleration is primarily performed by a brake control algorithm (BCA) contained within the brake control unit 310. The BCA processes the wheel speed, wheel acceleration, and brake pressure (hydraulic brake) or electric actuator (electric brakes) to calculate the braking pressure/force best suited for the most desirable braking. This may reduce a skid to recover a more efficient braking or short stopping distance. The resulting braking commands (e.g. pressure or force) may tend to minimize skids and cause braking commands to achieve efficient brake operation and short aircraft stopping distance. The resulting braking commands may correspond to gentle braking conditions to achieve smooth braking.

The wheel speed may be the actual measured speed of the wheel. In various embodiments, each wheel on aircraft 100 may be equipped with a wheel speed sensor 322, 324, 326, 328. However, in various embodiments, aircraft 100 may comprise a wheel speed sensor on any braked wheel. Wheel speed sensors 322, 324, 326, 328 may transmit (such as via a wired coupling) the wheel speed data to brake control unit 310. Brake control unit 310 may calculate a reference wheel speed for each wheel. The reference wheel speed may be the over ground speed that the wheel would be travelling if the wheel were rolling without slipping. For example, if wheel speed sensor 322, 324, 326, 328 measures a wheel speed of 10 radians per second for a wheel with a radius of 1 meter, brake control unit 310 may calculate a reference wheel speed of 10 meters per second. During spin up and subsequent braking, wheels may be at least partially slipping. Thus, the wheel reference speed may be different from the actual speed of aircraft 100 during spin up and braking events. The BCA may process wheel speed measurements which results in a wheel reference speed. The wheel reference speed may be set equal to the wheel speed during initial portions of a landing stop. The BCA wheel reference calculations are designed to estimate the aircraft speed rejecting the wheel speed effects of skidding, spin ups, and/or the like. A skidding or slipping wheel (after the key slip velocity threshold) produces less drag force. Thus, the aircraft is decelerated less but the wheel reference reflects the aircraft speed, not the wheel speed. Wheel reference speeds are estimations of aircraft speed and separate more from the wheel speed as a skid grows deeper.

Processor 312 may map the measured wheel speed measurements to aircraft 100 position data on runway 50 to determine an estimate of the coefficient of friction for portions of runway 50 and/or the slip ratio of the wheel. A skid may occur as the applied brake torque exceeds the available spin up torque created from the tire/runway interface friction. Processor 312 may utilize a measured wheel speed, calculated acceleration, wheel reference and tire normal force estimation mapped to aircraft 100 position data on the runway 50 to determine an estimate of the coefficient of friction and/or the slip ratio as a function of position. In response to braking stops that involve the anti-skid function, peak wheel accelerations may be used to estimate a peak coefficient of friction (see FIG. 4). The wheel speed and wheel reference may be used to estimate slip ratio. The peak wheel acceleration and tire normal force may be used to estimate the coefficient of friction. The slip ratio value corresponding to the peak coefficient of friction may define the peak slip ratio. In response to braking stops that do not involve the anti-skid function, measured wheel speed, calculated acceleration, wheel reference, and tire normal force estimation may be used to estimate a lower bound of the wheel slip value and/or coefficient of friction.

In response to a slow speed threshold (such as wheel speed sensor dropout (about 10 kts, about 18.52 Km/hr)) an estimate of aircraft 100 weight is obtained and the instantaneous runway 50 friction property may be calculated for each of the braked wheels as a function of aircraft 100 position data (previously recorded, such as by location sensor 330). A slow speed threshold may involve the aircraft being free from forces which would alter the tire normal forces. Estimating the weight of the aircraft may involve determining a tire pressure of a tire of the first braked wheel and calculating the weight of the aircraft based on the determined change tire pressure from a known reference value. This is coupled with the distance between the aircraft touchdown position and low speed threshold condition position. The tire pressure sensor helps with the identification of the spring constant to associate with the tire and the distance and assists the identification of the tire radius. Aircraft position may be ascertained more than once after or before wheel speed sensor drop out to verify tire radius. This may assist with the estimation the tire normal force which is used to calculate the friction property data. This calculation may be done "after-the-fact" as an accurate aircraft 100 weight measurement cannot generally be obtained during the landing due to transient lift and aircraft pitching due to braking. This may include but is not limited to the aircraft pitching which may occur during antiskid cycling. For instance, at certain speeds, lift from the wings may substantially affect a weight measurement. Thus, this after-the-fact calculation may be made in response to aircraft 100 traveling at a speed where there is no lift adversely affecting the calculation.

Runway 50 touchdown and/or a low speed threshold location data may be obtained from a position/location sensor 330, such as a GPS unit/receiver. The positioning data may be used in conjunction with a measured number of wheel rotations for each wheel. The wheel rotation count and the wheel radius may be used to estimate the absolute runway 50 positions; which, in turn, have associated slip and friction values (which may be calculated/extrapolated from the measured wheel speed, calculated acceleration, wheel reference and tire normal force estimation at those locations).

This information may be transmitted to a system external to aircraft 100 and made available for additional aircraft landing on runway 50. The findings of the actual location, e.g. portions of runway 50 traveled by aircraft 100, during a landing event, at various intervals may be aggregated with measured results of other aircraft having brake control system 101 to develop an expanded knowledge of runway 50 and its characteristics for a period of time. Brake control system 101 may create a moving average of the data to identify longer-term trends of the coefficient of friction and/or the slip ratio as a function of position. This expanded knowledge of runway 50 characteristics may be communicated to additional components of aircraft 100 and/or other aircraft in the vicinity or expected to be in the vicinity so that appropriate action may be taken.

In operation, in response to a touchdown associated with a landing on runway 50, wheel speed information is collected. Initially, each wheel is subject to a spin up condition, to bring the wheels up from substantially stationary to a rolling speed which is the same as aircraft 100 during landing. During this period, a touchdown protection phase is enacted so that no brakes are applied. In response to a wheel speed spin up and/or touchdown, a wheel reference value measurement is made. A wheel reference value may be an estimate of aircraft 100 speed measured at each wheel. The reference speed may be updated at any suitable time. For instance the reference speed may be continuously updated throughout the braking event and continues until low speed threshold condition. Thus, aircraft 100 equivalent speed which is the instantaneous wheel speed and wheel reference data may be initial quantities for brake control system 101. Initially these values should be substantially equivalent. In response to applying a brake, a drag force is generated. In turn, these values (e.g. the instantaneous wheel speed and the wheel reference value) separate. The brake pressure from sensors 342, 344, 346, 348 and/or the tire pressure from sensors 332, 334, 336, 338 may be measured at this time. Based on the friction generated, the rotation of each wheel relative to aircraft 100 speed is decreased. An aircraft reference speed is calculated/estimated and is calculated as a weighted combination of the individual wheel reference speeds.

Figure 4:
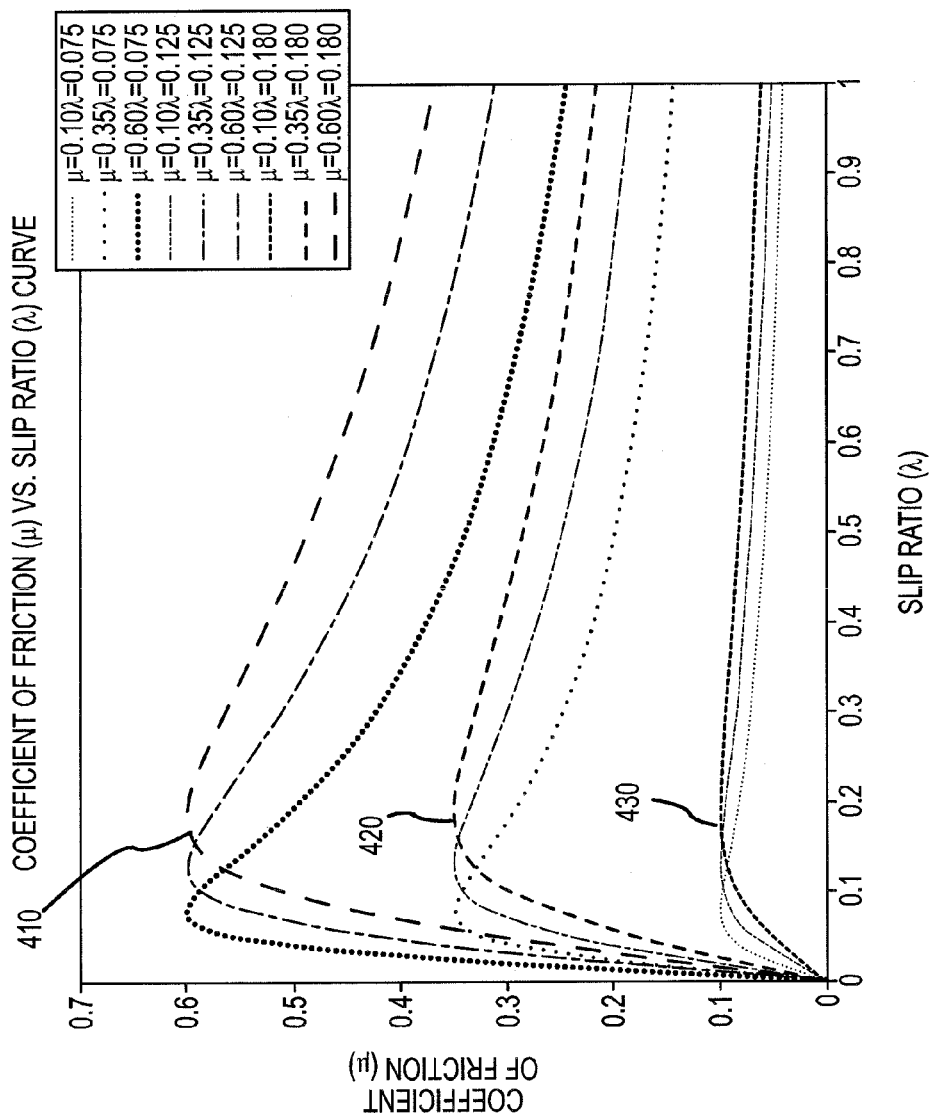
FIG. 4 illustrates, in accordance with various embodiments, a simplified graph depicting coefficient of friction vs. slip ratio curve.

Referring to FIG. 4, a graph depicting a coefficient of friction and/or the slip ratio according to various embodiments is presented. This data plotted at various times and/or positions may yield information regarding conditions of the runway and capacities of the braking system associated with those conditions. Varied runway conditions will affect the data. For instance, dry runway conditions may be associated with peak 410. Wet runway conditions may be associated with peak 420. Icy runway conditions may be associated with peak 430.

In response to measured brake pressure or brake actuator force, torque generated may be estimated. Brake pressure may be either increasing or decreasing. In response to the slip exceeding the key peak value the increasing brake pressure will result in decreasing drag force. A measured acceleration maximum during a period where aircraft 100 is generating wheel slips corresponds to the peak slip ratio as related in the coefficient of friction vs. slip relationship. Thus, in response to maximum accelerations being measured, an estimate of the slip ratio curve and the value of coefficient of friction associated with the slip ratio may be gleaned.

In response to this reduction in speed, a peak of a new slip curve may be crossed. Each peak, 410, 420, 430 may correspond to a peak acceleration. In association with a braking stop, constant cycling will create multiple estimated peaks for the coefficient of friction vs. slip ratio curve, and the threshold may be crossed multiple times and establish new peaks at various plotted locations.

The peak of the new slip curve may be a peak friction point given the slip ratio. In response to a braking stop where there is no skidding, (e.g. no anti-skid system event), a lower bound to a slip ratio, and/or a lower bound for the coefficient of friction may be established. This lower bound may establish that the wheel is at least capable of this much friction without a skid event. This information may be exploited by aircraft 100. Additional details regarding brake mapping data are disclosed in co-pending U.S. patent application Ser. No. 13/968,060, filed Sep. 6, 2013, and entitled "BRAKE CONTROL SYSTEM COMPRISING TIRE/RUNWAY FRICTION PROPERTY ESTIMATION MAPPING" having common ownership as the present application, the contents of which are hereby incorporated by reference in their entirety for any purpose.

Figure 5:
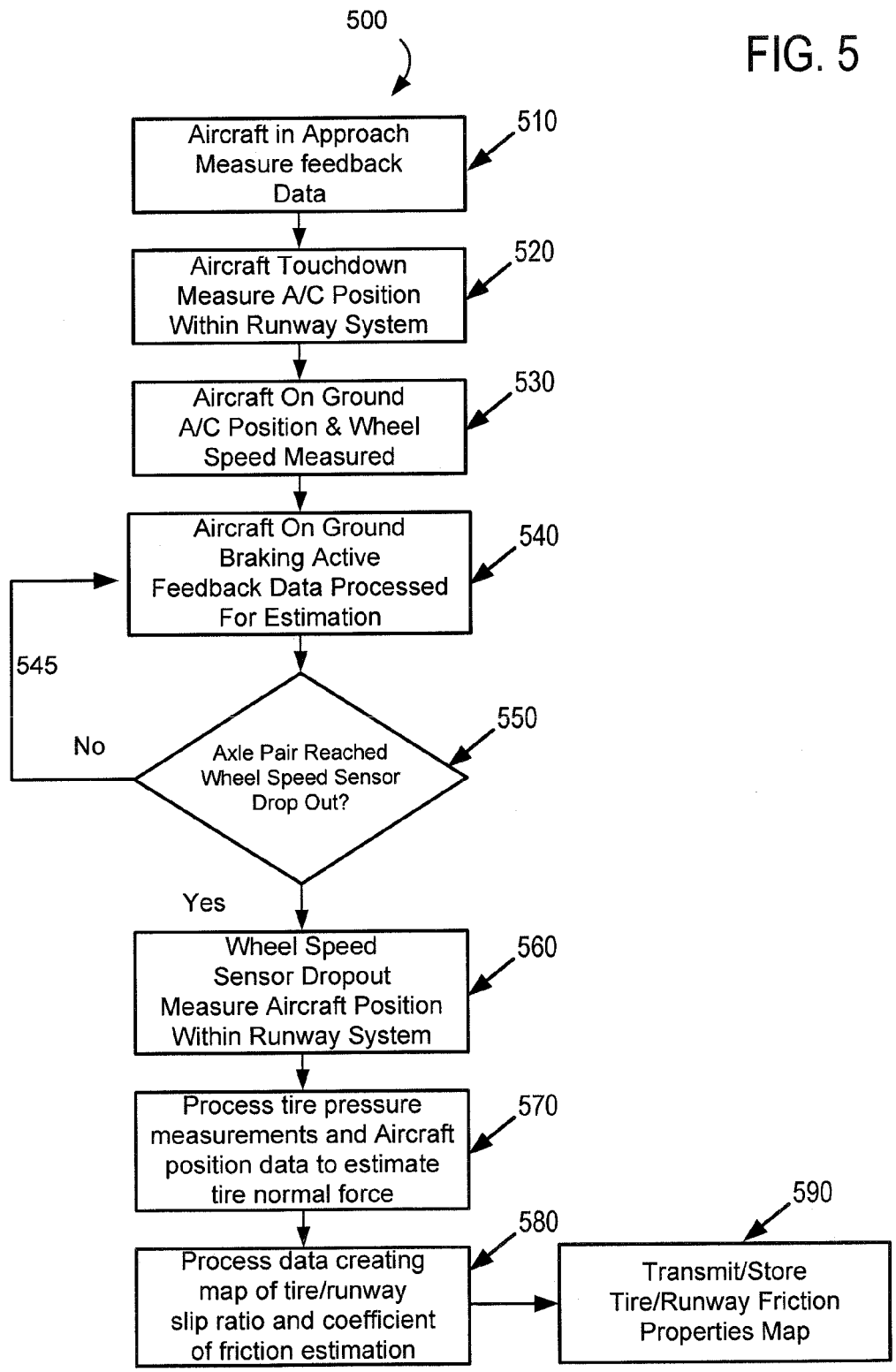
FIG. 5 illustrates, in accordance with various embodiments, a method for exploiting on ground wheel braking for estimation of a coefficient of friction vs. slip ratio curve.

Referring to FIG. 5, a process 500 for detecting an on ground characteristic is illustrated according to various embodiments. As aircraft 100 prepares for landing, brake control unit 310 may be in approach mode and measure feedback data (Step 510). In response to aircraft 100 landing, the wheels rotations may be spun up to aircraft 100 speed (Step 520). Aircraft position may be measured (Step 520). Brake control unit 310 may collect additional data in response to the landing. On ground position of the aircraft and/or wheel speed may be measured (Step 530). This may be done at any time and/or at any interval of time. On ground braking active data feedback may be processed for estimation (Step 540). A determination whether the axle pair has reached a wheel speed sensor drop out may be made. (Step 550). If not, return to step 540. (Step 545).

The low speed threshold (e.g., wheel speed sensor drop out speed) sensor may be associated with the aircraft position within the runway system (Step 560). Aircraft position may be measured (Step 560). The tire pressure measurements and aircraft position data may be used/processed to estimate tire normal force (Step 570). Data for creating a map of tire/runway slip ratio and coefficient of friction estimation may be processed (Step 580). The tire/runway friction properties may be transmitted and/or stored by the system (Step 590).

The reference wheel speed and the instantaneous wheel speed will begin to separate as the brakes are applied and friction is produced. These values may be compared by processor 312 utilizing one or more algorithms to determine a slip ratio as a function of aircraft position (Step 560). Acceleration maximums of the wheels may be noted as part of this process 500. A coefficient of friction may be determined/estimated as a function of position. These measured/estimated coefficient of friction values may be mapped to relevant portions of runway 50 (Step 580). Measured values and/or determinations may be stored to memory 314 and/or transmitted by transceiver 316. Note, the systems disclosed herein are applicable to braking during landing and/or during a rejected take-off braking stop.

According to various embodiments, the data collected and determined by system 300 may be processed into a useful form or application. One of these forms is the creation of a runway friction estimation map. This runway friction estimation map may be created by aggregating the determined estimated values captured by a plurality of aircraft landing events. This aggregated, synthesized runway friction estimation map data may be provided to an aircraft about to conduct braking or as braking is applied during a stop. This may reduce calculation time and result in quicker and more efficient braking.

Figure 6:
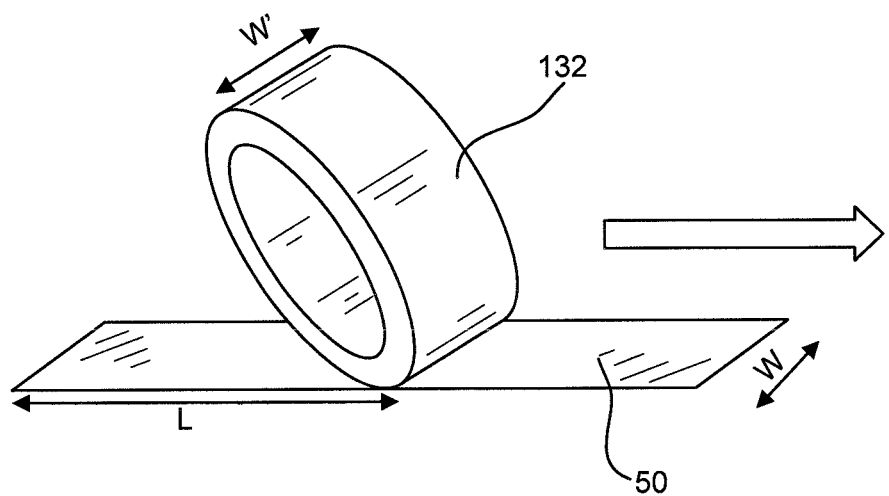
FIG. 6 illustrates, in accordance with various embodiments, an example of a friction element of a runway.

According to various embodiments, and with reference to FIG. 6, a runway 50 or taxiway may be divided into friction elements from end to end and side to side. A central runway friction estimation map may be a collection of adjacent friction elements which substantially completely cover the utilized portions of a runway or taxiway. As depicted in FIG. 6, a wheel, such as braked right outboard wheel 132, may travel down runway 50. Each friction element is a generally rectangular region based on the aircraft participating in the generation and use of the central friction estimation map. Generally, an individual friction element is a rectangle whose width, W, is substantially equal to the corresponding aircraft tire's contact patch, W'. The length, L, of each individual friction element may be substantially equal to the product of the period corresponding to the fastest antiskid cycling frequency (for example conditions associated with dry runway and maximum take-off weight conditions) and equivalent translational wheel speed or axel speed. The most accurate friction property estimation occurs once per complete skid cycle under antiskid control operation. The friction property estimation may then be assigned to the entire region contained within a single friction element.

Portions of the central synthesized friction estimation map may be based on the smallest friction element in the collected individual aircraft friction estimation map. The different friction elements associated with different aircraft are aggregated together and mapped onto a collection of base friction elements (corresponding to the smallest friction element) using simple relationships assuming data taken during the similar time frames. For example, mapping from larger friction elements to smaller friction elements can simply equate the friction properties for each smaller element whose geometric center lies within the larger friction element. Also, to map smaller friction element friction properties to larger friction element may involve mapping the weighted average of all smaller friction element's properties to the larger friction element if the smaller friction element's geometric center is contained within the larger friction element rectangle.

For instance, in response to an aircraft 100 performing a braking stop (ex. landing stop or rejected take-off stop) the brake control unit associated with the BCA (as described above) may create a portion of the data to be utilized in a friction estimation map. This data to be utilized in a friction estimation map may be transmitted from the aircraft 100 to the central database/friction map algorithm for processing.

Figure 8:
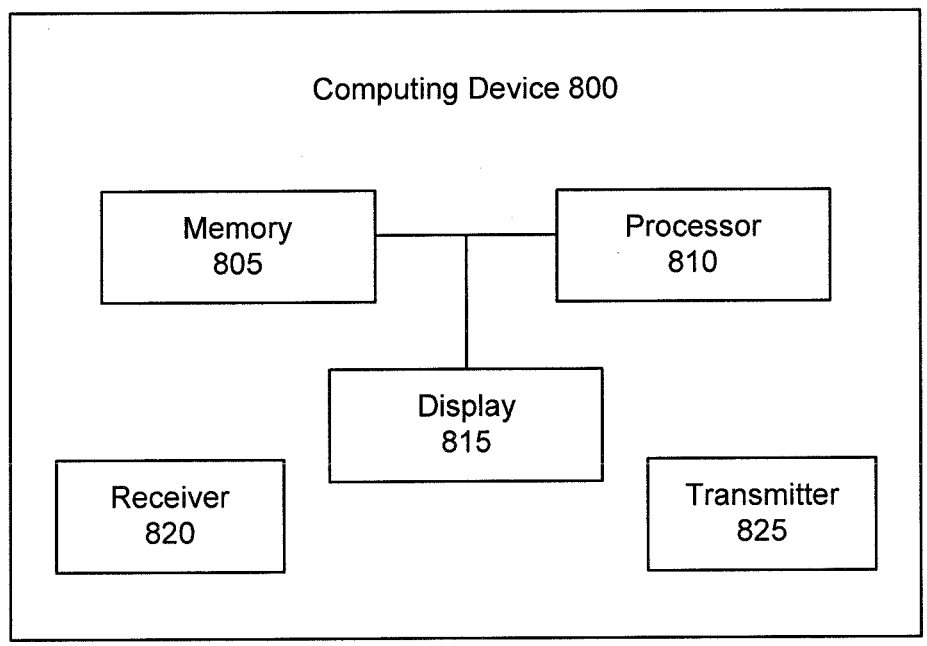
FIG. 8 illustrates, in accordance with various embodiments, a central database/central friction map (CFM) computing device 800.

With brief reference to FIG. 8, the central database/central friction map (CFM) processor may comprise a computing device 800 (e.g., processor 810) and an associated memory 805. The memory 805 may comprise an article of manufacture including a tangible, non-transitory computer-readable storage medium having instructions stored thereon that, in response to execution by a computing device 800 (e.g., processor 810), cause the computing device 800 to perform various methods. The computing device 800 may be coupled to a transmitter 825, receiver 820, transceiver, and/or network for sending and receiving data. The computing device 800 may be coupled to a display 815 configured to distribute data to a user.

The CFM processor may receive environmental data (ex. temperature, barometric pressure). The information of the CFM processor may undergo temporal weighting such that of successive friction estimation maps from aircraft braking stops may properly combined into a single representative friction estimation map for a runway 50. The CFM processor initially transfers the specific aircraft 100 friction property map data (friction properties and position data) onto a base friction elements template. After mapping this friction property vs. position data onto the friction elements, e.g. locations where the wheels traversed the runway 50, the CFM processor may perform spatial (ex. distance weighted) processing in order to fill-in and/or estimate the remainder of the friction elements.

The friction elements may be sized and located according to the aircraft producing the data. The friction elements may be mapped to the base friction elements (smallest sized friction elements in the collection of friction estimation maps). A time weighting method may be used to combine the collection of friction estimation maps created over time into a single representative friction estimation map. This process may be accomplished sequentially, such as a single friction element at a time, until all friction elements have been processed. For example, such filtering of friction element friction data will tend to de-emphasize older data in favor or more recent friction data. This temporal processing may be further enhanced through the influence of environmental weighting (e.g., significant changes in air temperature within the collection of friction estimation maps indicate different weighting for different friction estimation maps). Friction data having similar environmental metrics may be weighted more similarly than data with different metrics. The single representative friction estimation map having an average of data for appropriate regions (ex. brake application region immediately after touchdown, brake application regions appropriate for RTO stops) and/or position specific data may be available for transmission to other aircraft which can exploit this information.

The type of access to the CFM processor and the data acquired based on that access (average and specific position) may affect how the data is utilized. For instance, in traditional landing schema, aircraft performing braking without the benefit of friction estimation mapping interact with the runway 50 and assess performance metrics within the brake control algorithm (BCA) to converge to desired performance levels. Utilizing an average or representative information corresponding to the regions where the brakes will be initially applied affords the aircraft's 100 BCA the opportunity to use representative data to better initialize BCA controllers for the initial brake application region. For instance, an integrator or state of the BCA may be pre-set to a friction level that is closer to an observed or empirically derived friction level than having no known friction level. Utilizing friction property data corresponding to specific location and potentially throughout the entire braking stop (not just initial conditions) offers the aircraft's BCA the advantage of greater accumulated runway 50 knowledge.

Figure 7:
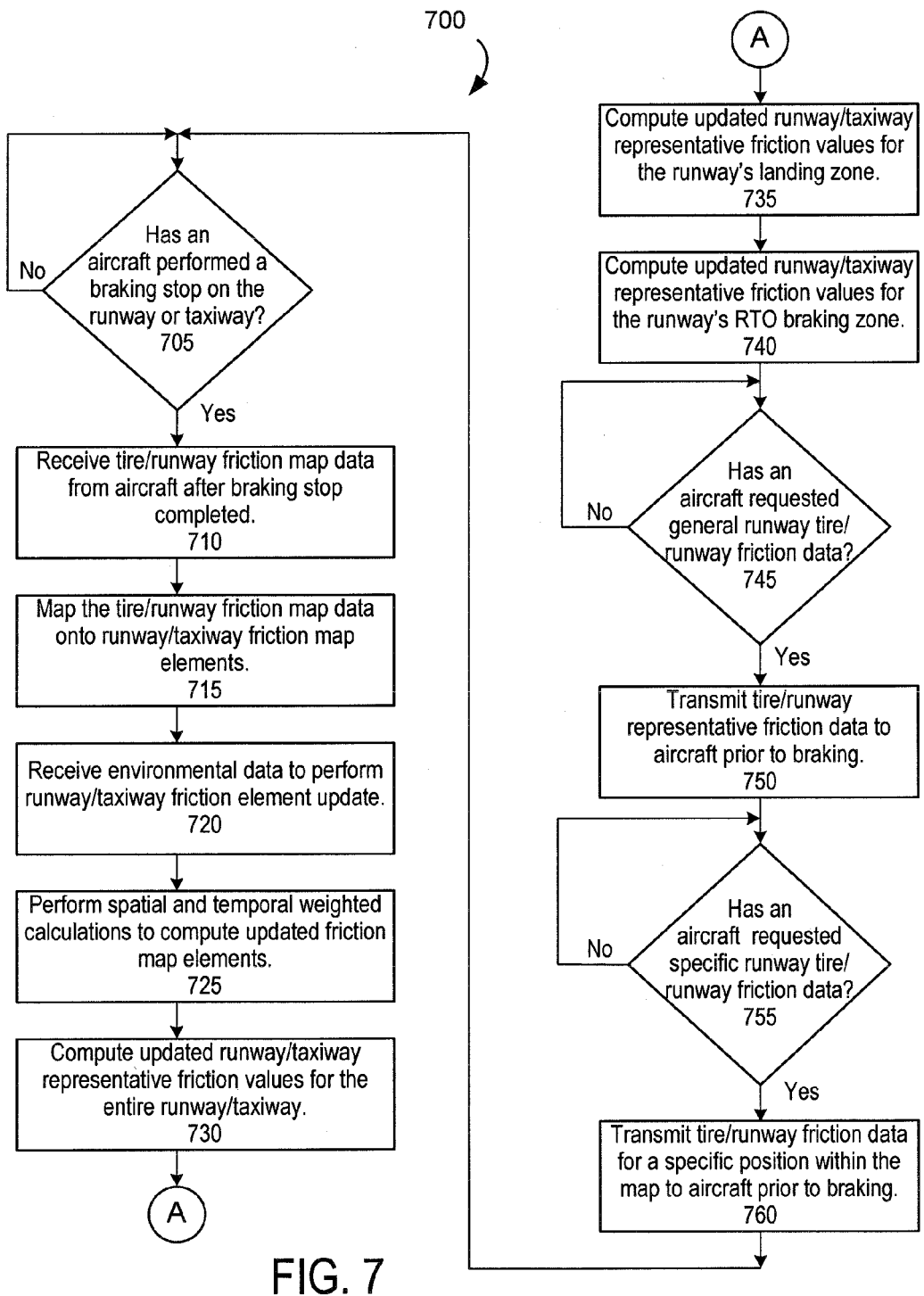
FIG. 7 illustrates, in accordance with various embodiments, a method for mapping coefficient of friction vs. slip ratio curve data.

With reference to FIG. 7, a method 700 for building a runway friction estimation map is disclosed. A determination that the aircraft has performed a braking stop on the runway or taxiway is made (step 705). Consistent with the prior disclosed methods, tire/runway friction estimation map data is received from the aircraft 100 in concert with a braking stop process, such as a braking stop being completed (step 710). The tire/runway friction estimation map data may be populated to runway/taxiway friction elements (Step 715). The CFM processor may receive environmental data to perform a runway 50 friction element update. The environmental data may be gathered from any source such as a weather providing system or on site sensors (step 720). Spatial and/or temporal weighted calculations may be performed to compute updates to friction elements (step 725). For instance, the system may determine relative wheel locations based on aircraft 100 position data. Also, the CFM processor may estimate unknown friction element data from known friction element data. For instance, a known friction element proximate to an unknown friction element may be utilized to estimate the unknown friction element. An average of known friction elements may be made to estimate an unknown friction element located between known friction elements. Older in time determinations of friction elements may be given less weight as compared to new friction element data. In this way, outdated data, such as due to changes in conditions due to weather, may be accounted. The CFM processor may process the updated runway/taxiway representative friction element values for the entire runway/taxiway 50 (step 730).

The CFM processor may compute updated runway 50 representative friction element values for the runway's 50 landing zone (step 735). The CFM processor may compute updated runway 50 representative friction element values for the runway's 50 RTO braking zone (step 740). A determination may be made if an aircraft 100 requested general runway friction estimation map data (step 745). In response to an aircraft 100 making a general runway 50 friction estimation map data request, representative friction estimation map data may be transmitted to the aircraft 100 prior to braking (step 750). General tire/runway friction data may comprise an average value for a particular zone. A determination may be made that the aircraft 100 has requested specific runway tire/runway friction data (step 755). Specific tire/runway friction data may comprise substantially realtime based on a current position of a wheel. In response to the aircraft 100 making a specific runway 50 friction estimation map data request, representative friction estimation map data may be transmitted to the aircraft prior to braking (step 760).

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the inventions. The scope of the inventions is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

The term "coefficient of friction" as used herein may refer to the ratio of the force that maintains contact between an object and a surface and the frictional force that resists the motion of the object. The frictional force may be equal to the coefficient of friction multiplied by the normal force on the surface. Slip ratio as used here may refer to a means of calculating and expressing the locking status of a wheel. Slip Ratio %=[(Vehicle Speed−Wheel Speed)/Vehicle Speed]×100.

One skilled in the art will appreciate that the systems and methods disclosed herein may employ any number of databases in any number of configurations. Further, any databases discussed herein may be any type of database, such as relational, hierarchical, graphical, object-oriented, and/or other database configurations.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f), unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A system comprising:
   a tangible, non-transitory memory communicating with a central processor configured to aggregate coefficient of friction data, the tangible, non-transitory memory having instructions stored thereon that, in response to execution by the central processor, cause the central processor to perform operations comprising:
   receiving, by the central processor, determined coefficient of friction data for a first series of locations along a runway from a first aircraft of a plurality of aircraft;
   associating, by the central processor, the coefficient of friction data to runway friction estimation map elements;
   receiving, by the central processor, determined coefficient of friction data for a second series of locations along the runway from a second aircraft of the plurality of aircraft; and
   aggregating, by the central processor, the received determined coefficient of friction data for the first series of locations along the runway from the first aircraft and the coefficient of friction data for the second series of locations along the runway from the second aircraft into a friction estimation map for the runway; and
   performing, by the central processor, temporal calculations to form the friction estimation map, wherein the temporal calculations comprise weighting current data heavier than not current data for overlapping runway friction estimation map elements and updating the not current data with the current data for the overlapping runway friction estimation map elements to reflect a condition change on the runway over time.

2. The system of claim 1, further comprising performing, by the central processor, spatial calculations to form the friction estimation map.

3. The system of claim 2, wherein the spatial calculations comprise extrapolating a wheel position from a first aircraft position based on at least one of an aircraft type and a geometric setup of landing gear of the first aircraft.

4. The system of claim 2, wherein the spatial calculations comprise estimating unknown runway friction estimation map elements based on nearest neighbor known runway friction estimation map elements.

5. The system of claim 1, further comprising receiving, by the central processor, environmental data related to the condition change on the runway.

6. The system of claim 1, wherein the condition change reflected by the weighting comprises at least one of a decrease or an increase in air temperature.

7. The system of claim 6, wherein the decrease in air temperature reflects the presence of at least one of ice, snow, or water on the runway.

8. The system of claim 6, wherein the increase in air temperature reflects at least one of melting of ice, melting of snow, or evaporation of water from the runway.

9. A method comprising:
   receiving, by a computing device comprising a central processor and a tangible, non-transitory memory, coefficient of friction data of a first series of locations along a runway from a first aircraft;
   receiving, by the central processor, coefficient of friction data for a second series of locations along the runway from a second aircraft;
   associating, by the central processor, the coefficient of friction data to runway friction estimation map elements;
   aggregating, by the central processor, the received determined coefficient of friction data for the first series of locations along the runway from the first aircraft and the determined coefficient of friction data for the second series of locations along the runway from the second aircraft into a friction estimation map for the runway; and
   performing, by the central processor, temporal calculations to form the friction estimation map, wherein the temporal calculations comprise weighting current data heavier than not current data for overlapping runway friction estimation map elements and updating the not current data with the current data for the overlapping runway friction estimation map elements to reflect a condition change on the runway over time.

10. The method of claim 9, further comprising performing, by the central processor, spatial calculations to form the friction estimation map.

11. The method of claim 10, wherein the spatial calculations comprise extrapolating a wheel position from a first aircraft position based on at least one of an aircraft type and a geometric setup of landing gear of the first aircraft.

12. The method of claim 10, wherein the spatial calculations comprise estimating unknown runway friction estimation map elements based on nearest neighbor known runway friction estimation map elements.

13. The method of claim 9, wherein a length of an individual friction element is substantially equal to a product of a period corresponding to a fastest antiskid cycling frequency and an equivalent translational wheel speed, and a width of the individual friction element is substantially equal to a width of an aircraft wheel.

14. The method of claim 9, further comprising receiving, by the central processor, environmental data related to the condition change on the runway.

15. The method of claim 9, further comprising transmitting, by the central processor, the friction estimation map for the runway to a third aircraft for exploitation.

16. The method of claim 9, further comprising associating a time stamp with at least one of the received coefficient of friction data for the first series of locations along the runway from the first aircraft and the received coefficient of friction data for the second series of locations along the runway from the second aircraft.

17. The method of claim 9, wherein the condition change reflected by the weighting comprises at least one of a decrease or an increase in air temperature around the runway.

18. The method of claim 17, wherein the decrease in air temperature reflects the presence of at least one of ice, snow, or water on the runway.

19. The method of claim 17, wherein the increase in air temperature reflects at least one of melting of ice, melting of snow, or evaporation of water from the runway.

* * * * *